United States Patent [19]

Kirkpatrick et al.

[11] Patent Number: 4,498,467
[45] Date of Patent: Feb. 12, 1985

[54] ORTHOPEDIC CAST, DEVICE AND METHOD FOR FORMING SAME AND PACKAGE THEREFOR

[75] Inventors: Harold B. Kirkpatrick, 349 Silver Hill Rd., Easton, Conn. 06612; Fred A. Ravreby, 56 Knight Rd. Extension, Framingham, Mass. 01701; Henry L. Richbourg, Statesville, N.C.

[73] Assignees: H. B. Kirkpatrick, Easton, Conn.; F. A. Ravreby, Framingham, Mass.

[21] Appl. No.: 341,190

[22] Filed: Jan. 20, 1982

[51] Int. Cl.³ .................................................. A61F 5/04
[52] U.S. Cl. ........................................ 128/90; 206/219
[58] Field of Search ..................... 128/89, 90, 156; 206/219

[56] References Cited

U.S. PATENT DOCUMENTS

| | | | |
|---|---|---|---|
| 1,351,441 | 8/1920 | Pond | 206/219 |
| 2,218,844 | 10/1940 | Lovell | 128/90 |
| 2,700,461 | 1/1955 | Smith | 128/90 |
| 2,874,830 | 2/1959 | Birmingham, Jr. | 128/90 |
| 3,343,664 | 9/1967 | Poitras | 206/219 |
| 3,373,741 | 3/1968 | Hill et al. | 128/90 |
| 3,375,822 | 4/1968 | Rose | 128/90 |
| 3,674,021 | 7/1972 | Snyder et al. | 128/90 |
| 3,958,728 | 5/1976 | Nienart | 222/519 |
| 3,990,683 | 11/1976 | Ravreby | 206/219 |
| 4,131,114 | 12/1978 | Kirkpatrick et al. | 128/90 |
| 4,153,052 | 5/1979 | Tsuk | 128/90 |
| 4,289,233 | 9/1981 | Firth | 206/219 |
| 4,376,438 | 3/1983 | Straube et al. | 128/90 |
| 4,442,833 | 4/1984 | Dahlen et al. | 128/90 |
| 4,450,833 | 5/1984 | Brooks et al. | 128/90 |

Primary Examiner—C. Fred Rosenbaum
Assistant Examiner—Harrie S. Samaras
Attorney, Agent, or Firm—Toren, McGeady and Stanger

[57] ABSTRACT

A device for forming an orthopedic cast is disclosed which is composed of a core having a fibrous, porous tape rolled thereabout. The tape is impregnated with a first liquid component of a two-component hardenable system. The core is composed of a pressure rupturable container having the second component of the two-component system therein in liquid form. The entirety is encased in a flexible package which serves as a mixing chamber for intermixing the first and second components upon application of pressure to the package sufficient to rupture the core. After intermixing, the package is opened, the tape unrolled and placed about the broken limb in the conventional manner. The cast hardens within a short time at ambient temperature to provide a light-weight, breathable and waterproof orthopedic cast.

47 Claims, 1 Drawing Figure

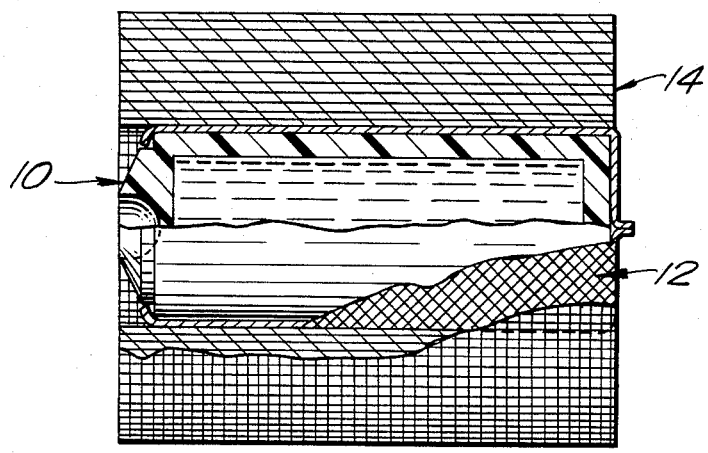

ORTHOPEDIC CAST, DEVICE AND METHOD FOR FORMING SAME AND PACKAGE THEREFOR

BACKGROUND OF THE INVENTION

1. Field of the Invention

This invention relates to orthopedic casts and devices for making same.

2. Description of the Prior Art

Numerous attempts have been made to produce a light weight, waterproof and breathable, i.e., air permeable, orthopedic cast which can be readily and easily fabricated by the physician and applied to the patient. The disadvantages of the conventional plaster of paris casts are well known, i.e., such casts are relatively heavy, have little or no resistance to water, i.e., disintegrate when wet, and are not porous to air or water vapor, i.e., have poor breathability. All of this makes them uncomfortable to wear. In particular, the poor breathability causes perspiration to accumulate on the patient's skin with consequential itching and maceration. Additionally, in the preparation of plaster of paris tapes for application as a cast, they must be saturated with water. This penetrates the underwrap which contributes to the maceration of the skin. Finally, such casts have poor X-ray transparency and generate considerable dust upon removal.

In order to avoid these disadvantages, attempts have been made to use two-component resin systems which are applied to fabric tapes and which can be cured either by water, catalysts, or ultraviolet irradiation.

The delivery systems for such two component hardenable materials have presented problems. In the attempt to fashion devices which would maintain the components apart from one another until the actual time of use and then provide a mechanism for mixing of the components and impregnation of the tape, rather complicated mechanisms have been developed. Such a device is disclosed in U.S. Pat. No. 4,131,114. This patent also outlines the other attempts of the prior art to create comparable systems for this purpose.

The hardening or curing of such resins has also produced problems. For example, for those systems which are UV curable, relatively expensive UV irradiation equipment is required making the economics of such UV curable resin systems unfavorable. Also, such equipment is relatively large and takes up costly space in the limited area of the casting room. Urethane systems are also known which are formed from urethane prepolymers and which are water cured. These have limited water resistance, poor molding properties and cure too slowly. Consequently, such systems are not satisfactory substitutes for plaster of paris for the rapid immobilization of fractures and are not used as primary cast systems, but rather, as secondary casts after healing has started. Also, the systems, in practice, are used with relatively large amounts of excess water, which creates the same problems as encountered with plaster of paris.

Systems using two different resin components in micro-encapsulated form are also known. But these are expensive to manufacture and require special mechanical or radiation equipment.

Other synthetic resin systems proposed involve the use of thermoplastic polymers. Tapes impregnated with the thermoplastic material are immersed in a tank of water at a sufficiently high temperature to soften the material and allow the tape to be applied. This is disadvantageous since a tank of temperature controlled water is required. Also, because of the presence of the water, the underwrap becomes wet and results in the same problems as with plaster of paris. Such thermoplastic resins exhibit limited heat resistance, poor molding characteristics and harden too slowly for rapid immobilization of fractures. As a result, the use of such materials has been primarily limited to use as cast replacements after healing is well advanced. These are relatively heavy, bulky and of coarse construction. Additionally, these plastic systems which are based on caprolactone are prepared for application by heating in a water bath at a temperature which substantially exceeds tolerable levels without the protection of insulated gloves.

SUMMARY OF THE INVENTION

We have discovered a novel system for formation of a light-weight, breathable and waterproof resinous orthopedic cast which can be readily and easily fabricated and applied by the physician. The cast system of the present invention avoids the complex mixing and delivery systems of the prior art. Also, unlike plaster of paris and other casts prepared from polymeric materials, the device of the present invention is completely self-contained and requires no ancillary facilities for its preparation, such as, water reservoirs, etc. Furthermore, the components utilized provide a resin system which avoids discomfort to the patient during curing, is room temperature curable, does not require irradiation, so that complex UV equipment is not required, and is fully satisfactory with respect to not interfering with the air and/or water vapor permeability of the tape used for the cast.

Furthermore, orthopedic casts made from the system of the present invention are both solvent and water resistant. Thus, patients can swim and bath while wearing the cast.

An additional advantage of the cast system of the present invention is that the final cast is completely transparent to X-rays. This is important for observing the degree of healing, particularly in the case of hairline fractures and avoids the necessity of cast removal for this purpose. Further, being self-contained, the cast of the present invention is eminently suitable for use in the field in the treatment of accident victims and by the armed forces in applying casts to personnel injured in training or combat. Thus, the cast can be made to cure rapidly under conditions of extremely low ambient temperatures. The cast is so thin and finely textured that it can be worn easily and comfortably beneath outer garments. It does not develop the excessive tack or stickiness characteristic of polymeric water cured casts. Finally, the cast of the present invention cures so rapidly and molds so readily that it can be used as a substitute for the fastest curing plaster of paris in the immobilization of fractured limbs. This feature renders it superior to other synthetic casts, which, being slower to cure and difficult to mold, are rarely used as primary casts by orthopedic surgeons. Because it is also completely water resistant and of higher impact and crushing strength than plaster of paris, as well as being fully X-ray transparent, it serves to substantially reduce the need for and the incidence of subsequent recasting. This feature significantly reduces the costs to the patient.

More particularly, the device of the present invention is composed of a fibrous porous tape rolled about a core.

The tape is impregnated with a first liquid component of a two-component ambient temperature hardenable system and the core is composed of a sealed liquid impermeable pressure rupturable container which contains the second component of said hardenable two-component system in liquid form. This second component is a material which, on wetting the component impregnated in the tape, reacts to form a hard polymer or resin. The core with the impregnated tape therearound are together encased in a flexible sealed package. The package serves as a mixing chamber for intermixing the two components when pressure is applied to the package in order to rupture the core and release its contents. The package may thus be kneaded in order to thoroughly blend the two components. Thereafter, it is opened, the tape is unrolled, placed on the patient in the conventional manner, and allowed to harden in the desired position.

BRIEF DESCRIPTION OF THE DRAWINGS

The drawing is a view, partially in cross-section and partially in elevation, of a device in accordance with the present invention.

DESCRIPTION OF THE PREFERRED EMBODIMENT

As shown in the FIGURE, the device of the present invention includes a core designated as 10 which acts as a container for one part of a two-component hardenable system. The core may be generally cylindrical in shape although other shapes could be used. The core is fashioned from a material which is rupturable, preferably by hand pressure. Also, of course, the core should be liquid and gas impermeable so as to protect the contents thereof from either contamination, leakage or other deleterious effects. The core may be fashioned from wax, or a flexible polymeric film, e.g., polyethylene, polypropylene, polyvinyl chloride, polyvinylidene chloride, mineral filled thermosetting resins, e.g., urea-formaldehyde, phenolics, melamine formaldehydes, and the like, mineral filled thermoplastic resins, e.g., modified terephthalates, and the like. Of course, any material used must be inert to the chemical materials making up the active chemical components of the system. It is preferred that the core be formed from a material sufficiently frangible so that it breaks into many fragments on rupture.

The core is completely encased in a loosely fitting net-like stocking 12. Preferably, stocking 12 is formed from a knitted synthetic fiber. The apertures of stocking 12 are large enough to allow the liquid from core 10 to pass through but sufficiently small to retain the fragments of the ruptured core.

A resin impregnated fibrous tape 14 is wrapped around the thus encased core. Tape 14 may be knitted, woven, or non-woven from natural, synthetic or glass fibers which would suitably be used for fashioning into an orthopedic cast. Obviously, any type of woven, non-woven, or knitted fabric in the form of a tape having sufficient strength and which does not react deleteriously with the components used or does not detrimentally affect the skin, could be suitable for use as the tape. The tape should be sufficiently porous to provide the desired air permeability when it is finally cured into a cast. Typically, a loosely knitted or woven fabric will provide the desired properties.

The core 10 and stocking 12 with the impregnated tape 14 therearound are encased in a sealed package composed of an appropriate film material, not shown. The film should be flexible so as to facilitate squeezing of the package in order to rupture the core and thus allow the hardening component in the core to mix with the component in the tape. Further, the package material should be sufficiently strong to allow kneading of the entire tape so as to thoroughly mix the liquid from the ruptured core throughout the tape. One of the advantages of the present invention is that the high shear, intensive mixing necessary in conventional urethane systems is not required. This is because the fibers of the tape are covered with a relatively thin film of the first component resulting in high surface to volume ratio. This facilitates complete and uniform reaction of the two components by merely wetting the tape with the second component. Additionally, of course, the packaging material, while it should be strong enough to withstand the kneading to effect the above-noted wetting, must also be capable of being readily opened when desired to withdraw the thoroughly saturated tape therefrom for application to a patient. A variety of such quick opening devices are known. Suitable materials for the package include foil-film, laminated film, and the like.

In one embodiment of the present invention, the tape is wet with a polyol which may contain up to about 50 percent by weight plasticizers. It is also desirable to include an antifoaming agent, e.g., a polysiloxane, in the polyol to prevent any foaming which may occur during application of the tape. The amount of such antifoaming agent is generally in the range from 0.50 to 0.75 percent by weight of the total composition. A catalyst is also present in the polyol in an amount from about 0.1 to 3.0 weight percent of the total composition, depending on the catalyst used. The core contains an isocyanate which may also contain from about 0 to 30 weight percent plasticizer based on the total weight of the core content.

A variety of polyoxyalkylene polyols may be used. Typically, such polyoxyalkylene polyols are obtained from the reaction of a multi-functional alcohol with an alkylene oxide. Preferably, the polyoxyalkylene polyol is the reaction product of a dihydric or trihydric alcohol, such as, glycerine, diethylene or triethylene glycol, butylene glycol or any polyalkylene glycol and especially those having 2 to 4 carbon atoms in the alkylene groups, and an alkylene oxide, preferably having 2 to 4 carbon atoms in the molecule, such as, ethylene oxide, propylene oxide, or butylene oxide. Particularly preferred is the reaction product of glycerine and propylene oxide, the material having a molecular weight of about 260 and a hydroxyl number in the range from 644 to 676. Certain polyols, i.e., amine modified polyols, do not require catalysts as described hereinafter.

A variety of plasticizers may be used. Typical of these are short chain dialkyl phthalates, such as, dibutyl phthalate, and butyl benzyl phthalate. Acetyl tributyl citrate and dibutyl maleate may be used. Regardless of which plasticizer is used, it must be compatible with the polyol and any catalyst used, be non-toxic, and non-mutagenic, i.e., conform to the requirements of the various regulatory agencies; have a viscosity of less than about 50 cps, and preferably about 15 cps, be non-allergenic, not cause any skin sensitivity, and be colorless and odorless.

Isocyanates suitable for use include liquid isocyanates, for example, aromatic isocyanates, such as, tolylene diisocyanate (TDI), and aliphatic or cycloaliphatic isocyanates and, preferably, methylene diphenyl diisocyanate (MDI). The MDI may be modified in a known manner to make it a liquid at ambient temperatures, e.g., with a carbodiimide.

Catalysts used preferably include organo-metallic compounds, such as, organo-tin compounds, e.g., dibutyl tin dilaurate, amines, e.g., triethylene diamine, or metal salts of organic acids, e.g., calcium octoate. The amount of catalyst required is relatively small and the entire system possesses good shelf-stability.

The presence of the plasticizer appears to help prevent crystallization of the isocyanate making it possible to operate at lower temperatures.

Such polyols as well as prepolymers as discussed hereinafter and methods for preparation thereof are disclosed in U.S. Pat. No. 4,137,200, the contents of which are incorporated herein by reference.

In another embodiment of the present invention, the tape is impregnated with a urethane prepolymer composition which acts as one component of a room temperature curable resin system. Many such two-component hardenable systems are known to the artisan. A major requirement of such a hardenable system for use in the present invention is that the system, both with respect to its components as well as the final resin, cure or harden in a manner which is not deleterious to the patient so as to form a structurally sound cast member. As used herein, the term "prepolymer" means a system which has been partially polymerized but not cross-linked so as to be cured and which is in liquid or semi-liquid form. Preferred prepolymer compositions for use in the present invention may be composed of a polyol, a plasticizer, and an isocyanate.

The prepolymer, which may be diluted with plasticizers, is generally prepared by mixing the ingredients in the desired proportions and heating or "cooking" the mixture at a controlled temperature for a period of time sufficient to produce the desired isocyanate content. The progress of the reaction is followed by monitoring the free isocyanate concentration of the reaction mixture. The method for carrying out this process and measurement of the isocyanate content is well known. Generally, the reaction is terminated when the available isocyanate content of the reaction mixture is in the range from about 5 to 20%, and preferably is about 12%. The prepolymer should have a viscosity in the range from about 10,000 to 20,000 centipoise. By utilizing a prepolymer in this viscosity range, good adherence of the prepolymer to the tape and the desired proportions of prepolymer to tape can be effected. Of course, the entire process, i. e., the preparation of the prepolymer as well as the impregnation of the tape should be carried out in the absence of moisture to avoid subsequent curing of the prepolymer. For this purpose, the tape should also be moisture free.

The liquid component which is the component contained within the core is generally composed of a polyol, a plasticizer and a catalyst. Usually, the polyol and the plasticizer will be the same as those described above and used in the prepolymer. In this system, most preferably, the plasticizer is present in an amount from about 4 to 5 parts to one part of polyol.

As an alternative, the core may contain water, with or without a polyol and/or catalyst. In such an embodiment, the amount of water used is relatively minimal, i.e., only sufficient to induce curing by wetting the tape. Consequently, soaking through of the underwrap and the concomitant problems arising therefrom, as described hereinabove, are avoided. It is preferred in this embodiment that the prepolymer be a hydrophilic type, e.g., those based on ethylene oxide rather than propylene oxide.

The hardening component in accordance with the present invention is generally prepared by simply mixing the components in the desired proportions at ambient temperature. The liquid hardening component should have a viscosity from about 1 to 200 centipoise. This is quite important inasmuch as the relatively low viscosity of the liquid hardening component allows thorough blending of the liquid hardening component with the first component in the impregnated tape. Most preferably, the amount of catalyst is present in an amount equivalent to about 2.0 to 4.0 weight percent based on the total weight of the final cured resin.

The amount of glass tape to prepolymer will generally be in the range from about 1.2 to 1 parts by weight glass to prepolymer ±5%.

Since the curing time is dependent on the temperature as well as on the amount of catalyst, it is possible to customize the system to the particular ambient conditions under which it might be used. Thus, for low temperature conditions, increased amounts of catalyst would be used in the hardening component because the detrimental effect of lower temperatures can be offset by increased catalyst concentrations.

In the cast system of the present invention, the actual curing of the resin takes place in three distinct phases. The first stage occurs from the moment of mixing the components until the cast becomes tack free i.e., the resin composition is dry to the touch. This period is approximately 2 to 5 minutes. The second stage takes from about 3 to 10 minutes and is complete when the cast is sufficiently strong to immobilize the patient's limb. This end point can be identified in laboratory procedure by the resonant sound given off when it is struck by a metal rod. More precise quantitative measurements are made by destructive testing which record the psi at yield of a cylindrical test piece. The third stage takes about 30 minutes to 1 hour and is complete when the cast is weight bearing.

It is apparent that the device in accordance with the present invention can be made in different sizes to conform to specific orthopedic requirements, e.g., a wrist cast, arm cast, leg cast, etc. The present device is utilized by merely squeezing the outer package, usually with only hand pressure, and gently kneading the package for a short period of time, usually about 30 seconds to thoroughly blend and intermix the liquid hardening component throughout the impregnated tape roll. Thereafter, the outer package is opened, the tape removed, and wound or wrapped around the injured member in accordance with normal orthopedic procedures. Generally, of course, such cast preparation would be preceded by first placing a conventional synthetic fiber sleeve and underwrap or padding about the injured member in order to avoid direct contact with the skin and to provide comfort. The tape obtained from the device is then wrapped over this sleeve.

In the most preferred embodiment, the cast system of the present invention has the following formulations and tape pick-up weights (embodiment wherein core contains isocyanate and plasticizer and tape is coated with polyol/plasticizer/catalyst/antifoam composition):

| TAPE COMPONENT FORMULATION | | |
|---|---|---|
| | Optimal | Range |
| Polyol | 75.76% (wt) | 75.70%–75.80% |
| Dibutylphthalate | 20.91% (wt) | 20.85%–20.95% |
| Catalyst | 2.65% (wt) | 2.62%–2.68% |
| Antifoam | 0.68% (wt) | 0.66%–0.70% |

| CORE COMPONENT FORMULATION | | |
|---|---|---|
| | Optimal | Range |
| Diisocyanate | 89.78% (wt) | 89.73%–89.83% |
| Dibutylphthalate | 10.22% (wt) | 10.17%–10.27% |

| AVERAGE CHEMICAL WEIGHTS ON TAPE (4 yards) | | |
|---|---|---|
| | Optimal | Tolerance |
| 2 inches | 15 gm | 0.25 g |
| 3 inches | 22.5 gm | 0.25 g |
| 4 inches | 30 gm | 0.25 g |
| 5 inches | 37.5 gm | 0.25 g |
| Coating Ratio | 0.052 gm/in$^2$ | 0.002 |

| AVERAGE CHEMICAL WEIGHTS IN CORE | | |
|---|---|---|
| | Optimal | Tolerance |
| 2 inches | 24 gm | ±0.25 g |
| 3 inches | 36 gm | ±0.25 g |
| 4 inches | 48 gm | ±0.25 g |
| 5 inches | 60 gm | ±0.25 g |

In that embodiment wherein the tape is coated with a prepolymer, the most preferred formulation is as follows (The following weight relationships are for a knitted glass fiber tape 2 inches wide, 4 yards long and weighing 50 g. The formulation can be changed proportionately should a longer or shorter size tape be used.):

45 g of prepolymer formed by cooking 60 parts of 4,4-diphenylmethane diisocyanate with 10 parts of polyol to an available isocyanate content of 12½ percent (WITCO CASTOMER) are coated onto the tape. The tape is wrapped around a core which contains the following mixture:

36 g dibutyl phthalate,
9 g of a polyol which is the reaction product of glycerol and propylene oxide, and possesses a molecular weight of about 260 and a hydroxyl number of 644 to 676,
1.25 g of a catalyst composed of n-dibutyl tin dilaurate.

The following examples illustrate the present invention:

A series of casts were prepared using a variety of compositions in accordance with the present invention. The curing characteristics of each cast system were observed and are reported in Tables 1 and 2. For these tests, a 3 inch width woven glass fiber tape, 4 yards in length, is saturated with an appropriate mixture of the first and second components so that it is ready to undergo hardening. The specific compositions of the components are set forth in the tables.

Prior to the wrapping of the thus prepared tape, a 2¼ inch O.D. metal mandrel is covered with two layers of a stockinette, prepared from polypropylene monofilament to cover a 13 inch length along the mandrel. Two layers of a padded gauze underwrap are then wrapped over the stockinette to cover an 11 inch length along the mandrel. The ends of the stockinette are folded over the ends of the underwrap. A thermo-couple may be placed at the center of the assembly between the two layers of stockinette, if it is desired to measure the temperature during hardening. The saturated glass fiber tape is then wrapped over the underwrap as follows to form a cast having a 9 inch length:

(a) beginning at an appropriate point on the mandrel, e.g., one inch from the end of the underwrap (position 1), three fully overlapping wraps (perpendicular to the longitudinal axis of the mandrel);

(b) cross-diagonally and make a second three fully overlapping wraps (position 2) which are contiguous with the wrap at position (1);

(c) cross-diagonally again to make a third three fully overlapping wraps (position 3) which are contiguous with the wraps at position (2) (a nine inch length of the mandrel is covered);

(d) wrap diagonally back towards position (1), the wraps having a 50% overlap with one another, finishing at position 1.

The wrapped tape is then held in place by light hand pressure until it will maintain itself in position (1–3 minutes). A thermo-couple probe can also be placed at the surface of the thus formed cast. The cast is then allowed to harden (5 to 15 minutes) and removed from the mandrel for testing.

In the first series of tests, four casts were prepared in accordance with the present invention wherein the core component was an isocyanate mixed with a plasticizer and the tape component is a polyol and plasticizer in varying amounts. The curing of the cast was followed with temperature and time measurements. The results are set forth in Table 1.

TABLE 1

| Tape Composition (g)* | | Core Composition (g) | | Tack Time (min) | Ex. Peak Surface | Ex. Peak Interior | Tack-free (min) | Immobil (min) | Work Time (min) |
|---|---|---|---|---|---|---|---|---|---|
| polyol | 17.14 | diisocyanate | 32.57 | 1½ | 129° F. | 112° F. | 4 | 7 | 2–2½ |
| dibutylphthalate | 4.71 | dibutylphthalate | 3.43 | | 2½ | 4 | | | |
| catalyst | .243 | | | | | | | | |
| antifoam | .054 | | | | | | | | |
| tape wt. | 78.22 | | | | | | | | |
| polyol | 17.65 | diisocyanate | 34.12 | 1½ | 130° F. | 110° F. | 4 | 5½ | 2–2½ |
| dibutylphthalate | 4.84 | dibutylphthalate | 3.36 | | 2½ | 4 | | | |
| catalyst | .251 | | | | | | | | |
| antifoam | .055 | | | | | | | | |
| tape wt. | 78.52 | | | | | | | | |
| polyol | 19.71 | diisocyanate | 37.45 | 1½ | 133° F. | 110° F. | 4 | 5½ | 2–2½ |
| dibutylphthalate | 2.71 | dibutylphthalate | 3.05 | | 2½ | 4 | | | |
| catalyst | .259 | | | | | | | | |
| antifoam | .082 | | | | | | | | |

TABLE 1-continued

| Tape Composition (g)* | | Core Composition (g) | | Tack Time (min) | Ex. Peak Surface | Ex. Peak Interior | Tack-free (min) | Immobil (min) | Work Time (min) |
|---|---|---|---|---|---|---|---|---|---|
| tape wt. | 78.54 | | | | | | | | |
| polyol | 19.39 | diisocyanate = | 36.84 | 1¾ | 130° F. | 112° F. | 4 | 5 | 2–2½ |
| dibutylphthalate | 4.00 | dibutylphthalate = | 3.16 | | 2½ | 4 | | | |
| catalyst | .259 | | | | | | | | |
| antifoam | .081 | | | | | | | | |
| tape wt. | 78.61 | | | | | | | | |

Tack Time = period of time that cast remains tacky to touch.
Ex. Peak = peak exotherm or maximum temperature reached during cure.
Tackfree = period of time until cast is tackfree to touch.
Immobil = period of time after which cast is sufficiently set so as to immobilize.
Work Time = period of time during which cast is sufficiently flexible to be set in desired configuration.
*The tape was dried at temperatures in excess of about 325° F. to remove occluded water.

The polyol is the reaction product of glycerol and propylene oxide, possesses a molecular weight of about 260 and a hydroxyl number of 644 to 676 (Dow Voranol 2025).

The isocyanate used was 4,4'-diphenylmethane diisocyanate (Upjohn Isonate 143L).

The catalyst used was a 33% solution of 1,4-diazabicyclo-[2,2,2]-octane triethylenediamine in propylene glycol (Air Products DABCO 33).

The antifoam used was a commercial silicone antifoam, i.e., 100% silicon filled polydimethyl siloxane (Dow Corning 1500).

The dibutyl phthalate used was Reichhold STA-FLEX 48-550.

A second series of casts were prepared according to that embodiment of the invention wherein the core component is composed of a polyol containing a catalyst and the tape was impregnated with a prepolymer and plasticizer composition. The casts were prepared in the same manner as described above and after a cure time at an ambient temperature of 24 or 48 hours, were subjected to transverse crushing tests using a Scott tester (two platens—ambient temperature). The compositions of the two components and the crush results at first yield are set forth in Table 2.

TABLE 2

| 1  | A | 3.90 g  | Transverse crush     |
|    | B | 19.50 g | test 24 hr           |
|    | C | 1.10 g  | 1st yield = 310 lb   |
|    | D | 39.00 g |                      |
|    | E | 54.00 g |                      |
| 2  | A | 3.90 g  | Transverse crush     |
|    | B | 23.40 g | test 24 hr           |
|    | C | 1.10 g  | 1st yield = 225 lb   |
|    | D | 39.00 g |                      |
|    | E | 54.00 g |                      |
| 3  | A | 4.08 g  | Transverse crush     |
|    | B | 16.35 g | test 24 hr           |
|    | C | 1.10 g  | 1st yield = 240 lb   |
|    | D | 39.00 g |                      |
|    | E | 54.00 g |                      |
| 4  | A | 3.94 g  | Transverse crush     |
|    | B | 19.80 g | test 24 hr           |
|    | C | 1.13 g  | 1st yield = 360 lb   |
|    | D | 39.00 g |                      |
|    | E | 54.00 g |                      |
| 5  | A | 3.93 g  | Transverse crush     |
|    | B | 19.85 g | test 24 hr           |
|    | C | 1.08 g  | 1st yield = 260 lb   |
|    | D | 39.00 g |                      |
|    | E | 54.00 g |                      |
| 6  | A | 7.78 g  | Transverse crush     |
|    | B | 38.90 g | test 24 hr           |
|    | C | 1.10 g  | 1st yield = 262 lb   |
|    | D | 39.00 g |                      |
|    | E | 54.00 g |                      |
| 7  | A | 7.8 g   | Transverse crush     |
|    | B | 11.37 g | test 48 hr.          |
|    | C | 0.85 g  | 1st yield = 280 lb   |
|    | D | 39.00 g |                      |
|    | E | 54.00 g |                      |
| 8  | A | 3.90 g  | Transverse crush     |
|    | B | 15.14 g | test 48 hrs          |
|    | C | 1.10 g  | 1st yield = 298 lb   |
|    | D | 39.00 g |                      |
|    | E | 54.00 g |                      |
| 9. | A | 7.95 g  | Transverse crush     |
|    | B | 7.86 g  | test 48 hr           |
|    | C | 1.06 g  | 1st yield = 307 lb   |
|    | D | 39.00 g |                      |
|    | E | 54.00 g |                      |
| 10 | A | 6.33 g  | Transverse crush     |
|    | B | 14.16 g | test 48 hr           |
|    | C | 1.56 g  | 1st yield = 348 lb   |
|    | D | 39.00 g |                      |
|    | E | 54.00 g |                      |
| 11 | A | 6.00 g  | Transverse crush     |
|    | B | 12.00 g | test 48 hr           |
|    | C | 1.25 g  | 1st yield = 410 lb   |
|    | D | 39.00 g |                      |
|    | E | 54.00 g |                      |
| 12 | A | 8.96 g  | Transverse crush     |
|    | B | 35.95 g | test 48 hr           |
|    | C | 1.25 g  | 1st yield = 530 lb   |
|    | D | 44.80 g |                      |
|    | E | 54.00 g |                      |
| 13 | A | 4.48 g  | Transverse crush     |
|    | B | 17.98 g | test 48 hr           |
|    | C | 1.25 g  | 1st yield = 480 lb   |
|    | D | 44.80 g |                      |
|    | E | 54.00 g |                      |
| 14 | A | 3.32 g  | Transverse crush     |
|    | B | 16.74 g | test 48 hr           |
|    | C | 0.94 g  | 1st yield = 593 lb   |
|    | D | 44.80 g |                      |
|    | E | 54.00 g |                      |
| 15 | A | 4.67 g  | Transverse crush     |
|    | B | 20.97 g | test 48 hr           |
|    | C | 1.23 g  | 1st yield = 498 lb   |
|    | D | 44.80 g |                      |
|    | E | 54.00 g |                      |
| 16 | A | 4.48 g  | Transverse crush     |
|    | B | 17.90 g | test 48 hr           |
|    | C | 1.35 g  | 1st yield = 470 lb   |
|    | D | 44.80 g |                      |
|    | E | 54.00 g |                      |
| 17 | A | 4.51 g  | Transverse crush     |
|    | B | 20.14 g | test 48 hr           |
|    | C | 1.35 g  | 1st yield = 438 lb   |
|    | D | 44.80 g |                      |
|    | E | 54.00 g |                      |

A = polyol
B = dibutylphthalate
C = catalyst - dibutyl tin dilaurate
D = prepolymer formed by cooking 60 parts of 4,4-diphenylmethane diisocyanate with 10 parts of polyol to an available isocyanate content of 12½ percent (WITCO CASTOMER).
E = fiberglass tape

We claim:

1. A device for forming an orthopedic cast comprising:
   a fibrous porous tape rolled about a core, said tape being impregnated with a first liquid component of a two-component hardenable system; said core being composed of a sealed liquid impermeable pressure rupturable container and having therein a second component of said two-component hardenable system in liquid form which, on intermixing with said first component, reacts to form a hard resin at ambient temperatures; said tape and core being encased in a flexible package adapted to serve as a mixing chamber for intermixing the first and second components upon the application of pressure to said package sufficient to rupture the core.

2. The device of claim 1 wherein said core is cylindrical in shape.

3. The device of claim 1 or 2 wherein the tape is knitted or woven natural, polymeric or glass fiber.

4. The device of claim 1 or 2 wherein the core is composed of a material selected from the group consisting of paraffin wax, paraffin wax modified with polyethylene or mineral filled phenolic resin, urea resin, melamine resin, modified terephthalate resin, and polymeric film.

5. The device of claim 1 or 2 wherein the core is composed of a material selected from the group consisting of polyethylene, polypropylene, or polyvinylidine chloride.

6. The device of claim 1 or 2 wherein the first liquid component is a polyol and the second liquid component is an isocyanate.

7. The device of claim 1 or 2 wherein the first liquid component is a polyoxyalkylene polyol selected from the group consisting of the reaction products of a multi-functional alcohol and an alkylene oxide.

8. The device of claim 7 wherein the polyol is the reaction product of a dihydric or trihydric alcohol and an alkylene oxide said alkylene oxide having from 2 to 4 carbon atoms in the molecule.

9. The device of claim 7 wherein the multi-functional alcohol is selected from the group consisting of glycerine, diethylene glycol, triethylene glycol, and butylene glycol and the alkylene oxide is selected from the group consisting of ethylene oxide, propylene oxide, or butylene oxide.

10. The device of claim 7 wherein the polyol is the reaction product of glycerine and propylene oxide and possesses a molecular weight of about 260 and a hydroxyl number in the range from 644 to 676.

11. The device of claim 1 or 2 wherein the second liquid component is selected from the group consisting of aromatic, aliphatic and cycloaliphatic isocyanates.

12. The device of claim 1 or 2 wherein the second liquid component is selected from the group consisting of tolylene diisocyanate and methylene diphenyl diisocyanate.

13. The device of claim 1 or 2 wherein the first liquid component is a polyol and the second liquid component is an isocyanate and each component contains up to 50 weight percent and up to 30 weight percent, respectively, of a plasticizer.

14. The device of claim 13 wherein the plasticizer is selected from the group consisting of dibutyl phthalate, dibutyl maleate, butyl benzyl phthalate and acetyl tributyl citrate.

15. The device of claim 13 wherein the plasticizer is a short chain dialkyl phthalate.

16. The device of claim 1 or 2 wherein the first liquid component is a polyol and the second liquid component is an isocyanate and the polyol also contains from about 0.1 to 3.0 weight percent of a catalyst based on the weight of the polyol.

17. The device of claim 16 wherein the catalyst is selected from the group consisting of organo-tin compounds, amines, and metal salts of organic acids.

18. The device of claim 1 or 2 wherein the first liquid component is a prepolymer formed from a polyol and an isocyanate, said prepolymer having an available isocyanate content from about 5 to 20 percent and said polyol being selected from the group consisting of the reaction products of a multi-functional alcohol and an alkylene oxide.

19. The device of claim 18 wherein the polyol has a molecular weight of about 260 and a hydroxyl number from 644 to 676.

20. The device of claim 18 wherein the component within the core is composed of a polyol.

21. The device of claim 18 wherein the component within the core is composed of a polyol and a catalyst.

22. The device of claim 18 wherein the component within the core is composed of a polyol, a plasticizer and a catalyst.

23. The device of claim 22 wherein the plasticizer is selected from the group consisting of dibutyl phthalate, dibutyl maleate, butyl benzyl phthalate and acetyl tributyl citrate and the catalyst is selected from the group consisting of organo-tin compounds, amines, and metal salts of organic acids.

24. The device of claim 18 wherein the isocyanate is an aromatic, aliphatic or cycloaliphatic isocyanate.

25. The device of claim 18 wherein the second liquid component is water.

26. The device of claim 25 wherein the polyol is the reaction product of a dihydric or trihydric alcohol and an alkylene oxide said alkylene oxide having from 2 to 4 carbon atoms in the molecule.

27. The device of claim 25 wherein the multi-functional alcohol is selected from the group consisting of glycerine, diethylene glycol, triethylene glycol, and butylene glycol and the alkylene oxide is selected from the group consisting of ethylene oxide, propylene oxide, or butylene oxide.

28. The device of claim 25 wherein the polyol is the reaction product of glycerine and propylene oxide and possesses a molecular weight of about 260 and a hydroxyl number in the range from 644 to 676.

29. The device of claim 25 wherein the water contains a polyol.

30. The device of claim 29 wherein the water also contains a catalyst selected from the group consisting of organo-tin compounds, amines, and metal salts of organic acids.

31. A device for forming an orthopedic cast comprising a fibrous porous tape rolled about a core, said tape being impregnated with a polyol, said core being composed of a sealed liquid impermeable pressure rupturable container and containing a liquid isocyanate which, on intermixing with said polyol, reacts to form a hard resin at ambient temperatures, said tape and core being encased in a flexible package adapted to serve as a mixing chamber for intermixing the polyol and isocyanate upon the application of hand-pressure to the package sufficient to rupture the core.

32. A device for forming an orthopedic cast comprising a fibrous porous tape rolled about a core, said tape being impregnated with a polyol selected from the group consisting of the reaction products of a multi-functional alcohol and an alkylene oxide, said core being composed of a sealed liquid impermeable pressure rupturable container and containing a liquid isocyanate selected from the group consisting of aromatic, aliphatic and cycloaliphatic isocyanates, which, on intermixing with said polyol, reacts to form a hard resin at ambient temperatures, said tape and core being encased in a flexible package adapted to serve as a mixing chamber for intermixing the polyol and isocyanate upon the application of hand-pressure to the package sufficient to rupture the core.

33. A device for forming an orthopedic cast comprising a fibrous porous tape rolled about a core, said tape being impregnated with a polyol which is the reaction product of glycerine and propylene oxide and possesses a molecular weight of about 260 and a hydroxyl number in the range from 644 to 676, said core being composed of a sealed liquid impermeable pressure rupturable container and containing a liquid isocyanate selected from the group consisting of tolylene diisocyanate and methylene diphenyl diisocyanate, which, on intermixing with said polyol reacts to form a hard resin at ambient temperatures, said tape and core being encased in a flexible package adapted to serve as a mixing chamber for intermixing the polyol and isocyanate upon the application of hand-pressure to the package sufficient to rupture the core.

34. A device for forming an orthopedic cast comprising a fibrous porous tape rolled about a core, said tape being impregnated with a mixture of a polyol and up to about 50 weight percent of a plasticizer, said core being composed of a sealed liquid impermeable pressure rupturable container and containing a mixture of a liquid isocyanate and up to 30 weight percent of a plasticizer, which, on intermixing with said polyol, reacts to form a hard resin at ambient temperatures, said tape and core being encased in a flexible package adapted to serve as a mixing chamber for intermixing the polyol and isocyanate upon the application of hand-pressure to the package sufficient to rupture the core.

35. A device for forming an orthopedic cast comprising a fibrous, porous glass tape rolled about a core, said tape being impregnated with a composition composed of from 75.7–75.8 weight percent of a polyol which is the reaction product of glycerine and propylene oxide and possesses a molecular weight of about 260 and a hydroxyl number in the range from 644 to 676, from 20.85–20.95 weight percent of dibutylphthalate, from about 2.62 to 2.68 weight percent of a catalyst selected from the group consisting of organo-tin compounds, amines and metal salts of organic acids, and from about 0.66 to 0.70 weight percent of an antifoam agent, the amount of said composition on said tape being about 0.052 gm/in$^2$ ±0.25 g/in$^2$, said core being composed of a sealed liquid impermeable pressure rupturable container and containing a composition composed of from about 89.73 to 89.93 weight percent of methylene diphenyl diisocyanate modified with a carbodiimide so as to be a liquid at ambient temperature, and from about 10.17 to about 10.27 weight percent of dibutylphthalate, which core composition, on intermixing with said polyol, reacts to form a hard resin at ambient temperatures, said tape and core being encased in a flexible package adapted to serve as a mixing chamber for intermixing the polyol and isocyanate upon the application of hand-pressure to the package sufficient to rupture the core.

36. In a method for making an orthopedic cast for a limb wherein an underwrap is applied to the area of the limb and an immobilizing support is then formed by wrapping a fibrous, porous tape impregnated with a hardenable material around said underwrap and then hardening said hardenable material, the improvement which comprises said hardenable material being a two-component composition, the first component of which is a polyoxyalkylene polyol, and the second component of which is a liquid isocyanate, said composition being capable of hardening by mixing the two components at ambient temperatures, and wherein said tape is impregnated with a mixture of said two components which are then allowed to harden at ambient temperatures to form said cast.

37. The method of claim 36 wherein the first component is the reaction product of a multi-functional alcohol and an alkylene oxide.

38. The method of claim 36 wherein the polyol is the reaction product of a dihydric or trihydric alcohol and an alkylene oxide said alkylene oxide having from 2 to 4 carbon atoms in the molecule.

39. The method of claim 37 wherein the multi-functional alcohol is selected from the group consisting of glycerine, diethylene glycol, triethylene glycol, and butylene glycol and the alkylene oxide is selected from the group consisting of ethylene oxide, propylene oxide, or butylene oxide.

40. The method of claim 36 wherein the polyol is the reaction product of glycerine and propylene oxide and possesses a molecular weight of about 260 and a hydroxyl number in the range from 644 to 676.

41. The method of claim 36 wherein the second liquid component is selected from the group consisting of aromatic, aliphatic and cycloaliphatic isocyanates.

42. The method of claim 36 wherein the second liquid component is selected from the group consisting of tolylene diisocyanate and methylene diphenyl diisocyanate.

43. The method of claim 36 wherein the first component contains up to about 50 weight percent of a plasticizer and the second component contains up to 30 weight percent of a plasticizer.

44. The method of claim 36 wherein the first component contains up to about 50 weight percent of a plasticizer and the second component contains up to 30 weight percent of a plasticizer and the plasticizer is selected from the group consisting of dibutyl phthalate, dibutyl maleate, butyl benzyl phthalate and acetyl tributyl citrate.

45. The method of claim 36 wherein the first component contains a catalyst selected from the group consisting of organo-tin compounds, amines, and metal salts of organic acids.

46. The method of claim 36 wherein the first component contains a catalyst selected from the group consisting of organo-tin compounds, amines, and metal salts of organic acids in an amount from about 0.1 to 3.0 weight percent based on the weight of the polyol.

47. The method of claim 36 wherein the first component is a composition composed of from 75.7–75.8 weight percent of a polyol which is the reaction product of glycerine and propylene oxide and possesses a molecular weight of about 260 and a hydroxyl number in the range from 644 to 676, from 20.85–20.95 weight percent of dibutylphthalate, from about 2.62 to 2.68 weight percent of a catalyst selected from the group consisting of organo-tin compounds, amines and metal salts of organic acids, and from about 0.66 to 0.70 weight percent of an antifoam agent and the second component is a composition composed of from about 89.73 to 89.93 weight percent of methylene diphenyl diisocyanate modified with a carbodiimide so as to be a liquid at ambient temperature, and from about 10.17 to about 10.27 weight percent of dibutylphthalate.

* * * * *